United States Patent [19]

Durlach

[11] Patent Number: 4,563,470

[45] Date of Patent: Jan. 7, 1986

[54] N-SUBSTITUTED α,ωAMINO AND IMINO-SULFONIC ACID SALTS AND THEIR APPLICATION AS CATIONIC VECTORS OF HIGH CELLULAR PENETRATION

[75] Inventor: Jean P. Durlach, Paris, France

[73] Assignee: Les Laboratories Meram, Paris, France

[21] Appl. No.: 510,347

[22] Filed: Jul. 1, 1983

[30] Foreign Application Priority Data

Jul. 5, 1982 [FR] France ................................ 82 11768

[51] Int. Cl.$^4$ .................... C07D 213/67; A61K 31/44
[52] U.S. Cl. ...................................... 514/347; 546/294
[58] Field of Search ........................ 546/294; 424/263; 514/347

[56] References Cited

PUBLICATIONS

Raunio et al., Chemical Abstracts, vol. 83, No. 17, Abst. No. 146,652z, Oct. 27, 1975.
Chemical Abstracts, Ninth Collective Index, Chemical Substances, "Ethaneseleno-F", p. 15249CS, (1972–1976).
Burger, Medicinal Chemistry, pp. 823–24, Third Edition, Part II, Wiley-Interscience Pub., 1970.
Remington's Pharmaceutical Sciences, Fourteenth Edition, p. 794, Mack Pub. Co., 1970.
Raunio et al., "Spectral Properties of Schiff Bases Prepared from Pyridoxal . . . ", *Finn. Chem. Lett.;* 975, (1) 23–6.

*Primary Examiner*—Alan L. Rotman
*Attorney, Agent, or Firm*—Bacon & Thomas

[57] ABSTRACT

A salt of formula I or formula II

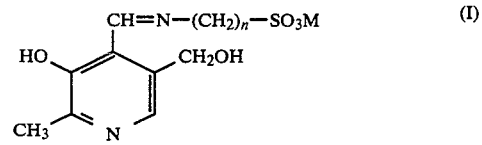

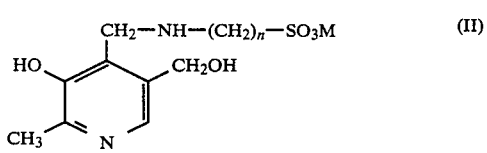

wherein n is 2 or 3 and M is an alkali metal or alkaline earth metal. Such compounds can be used to introduce the metal, e.g. magnesium, ion into cells to cure a deficiency thereof.

5 Claims, No Drawings

N-SUBSTITUTED α,ω-AMINO AND IMINO-SULFONIC ACID SALTS AND THEIR APPLICATION AS CATIONIC VECTORS OF HIGH CELLULAR PENETRATION

Taurine (2-aminoethanesulfonic acid) and homotaurine (3-aminopropanesulfonic acid) are two examples of α,ω-aminosulfonic acids which, in medicine, have shown little activity on oral administration.

It has been thought that, by preparing various derivatives of these amphoteric compounds having a polarity modified by N-substitution, it would be possible to obtain greater activity for α,ω-aminosulfonic acids on oral administration.

The method of preparation of these products does not allow the production of the sulfonic acids, but of the sulfonates. Quite surprisingly, an especial property of the alkali metal and alkaline earth metal salts of the amino-acids N-substituted by pyridoxyl has been discovered, as also for the imine intermediates in their synthesis. In attempting to modify the properties of the amino-acids, it has been discovered that the cations of the salts prepared have an unexpected property of particularly high penetration with respect to a subject, a property particularly desirable since the cations in the forms actually available therapeutically are of low activity, as is the case, for example, for magnesium salts.

The property conferred on N-pyridoxyl-substituted derivatives of the salts of α,ω-amino- (or imino-)ethane (and propane)-sulfonic acids is unique, since it is not found in a number of different N-substituted derivatives. While common to the group of compounds of the invention, it allows their use as vectors of their cations, and the different compounds according to the invention additionally possess, depending on their structure, in particular whether or not saturated, and according to the nature of their cations, the desired properties of each.

The invention has as its object the salts of the N-pyridoxylidene-imino-alkane-sulfonic acids of the formula

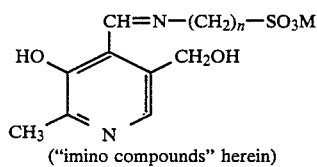

("imino compounds" herein)

and the N-pyridoxyl-amino-alkane-sulfonic acids of the formula

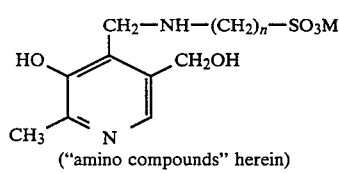

("amino compounds" herein)

in which n is 2 or 3 and M is an alkali metal (Na, K, Li, Rb, Cs) or an alkaline earth metal (Ca, Mg, Ba, Sr, etc.) and their use as medicaments.

By way of example, the preparation of sodium, potassium, calcium and magnesium salts of the 2-aminoethane- and 3-aminopropanesulfonic acids having N-pyridoxylidene and N-pyridoxyl substituents will now be described.

Alkali metal salts of the imino compounds, or Schiff bases, of the invention may be prepared by reacting the pyridoxal base with the salts of the α,ω-aminosulfonic acid, in the presence of a base, in an alcoholic medium. The imino derivative is then reduced to the corresponding amino compound using an alkali metal borohydride.

EXAMPLE 1

Sodium β-(3-hydroxy-5-hydroxymethyl-2-methyl-4-pyridylmethyleneimino)ethanesulfonate 20 cm³ water and 25 g (0.2 mole) taurine are added, with agitation, to 8 g (0.2 mole) soda. 300 cm³ absolute ethanol are then added to the solution thus obtained. The mixture is heated to 60° C. and 33.4 g (0.2 mole) finely ground pyridoxal base are added. The mixture is heated at 60° C. for 30 min. and the temperature is then allowed to decrease to 20° C. The yellow precipitate is dried, washed with 200 cm³ absolute ethanol and dried in a ventilated oven at 60° C., to obtain 55 g product. Yield 93%.

|  | ANALYSIS | | | |
|---|---|---|---|---|
|  | M.P. > 250° C. | | | |
|  | Soluble in water | | | |
|  | Insoluble in acetone and alcohol | | | |
| CALCULATED (%) | C = 40.5 | | FOUND (%) | C = 40.7 |
|  | H = 4.38 | | | H = 4.4 |
|  | N = 9.45 | | | N = 9.38 |
|  | S = 10.8 | | | S = 10.8 |

EXAMPLE 2

Sodium β-(3-hydroxy-5-hydroxymethyl-2-methyl-4-pyridylmethylamino)ethanesulfonate 29.6 g (0.1 mole) of the finely-divided product of Example 1 are added to 150 cm³ methanol. 1.8 g (0.05 mole) sodium borohydride are added, in small portions, with stirring, while maintaining the temperature at 20° C. After the borohydride is introduced, the mixture is stirred for 1 hour at 20° C., the insoluble matter filtered out and the filtrate concentrated to dryness. About 30 g of the product are obtained, which are recystallised in 2 volumes of methanol. After filtration, 25 g (84%) of white crystals are obtained.

|  | ANALYSIS | | | |
|---|---|---|---|---|
|  | M.P. > 250° C. | | | |
|  | Soluble in water | | | |
|  | Poorly soluble in methanol | | | |
|  | Insoluble in acetone | | | |
| CALCULATED (%) | C = 40.24 | | FOUND (%) | C = 41 |
|  | H = 5.03 | | | H = 4.95 |
|  | N = 9.39 | | | N = 9.41 |
|  | S = 10.73 | | | S = 10.8 |

EXAMPLE 3

Potassium β-(3-hydroxy-5-hydroxymethyl-2-methyl-4-pyridylmethyleneimino)ethanesulfonate 10 cm³ water and 12.5 g (0.1 mole) taurine are added, with agitation, to 5.6 g (0.1 mole) potash. 150 cm³ absolute ethanol are then added to the solution thus obtained. The mixture is heated to 60° C. and 16.7 g (0.1 mole) finely-ground pyridoxal base are added. The mixture is heated at 60° C. for 30 min. and the temperature is then allowed to decrease to 20° C. The yellow precipitate is dried, washed with 100 cm$^3$ absolute ethanol and dried in a ventilated oven at 60° C., to obtain 27.7 g product. Yield 89%.

| ANALYSIS | | | |
|---|---|---|---|
| M.P. > 250° C. | | | |
| Soluble in water | | | |
| Insoluble in acetone | | | |
| CALCULATED (%) | C = 38.46 | FOUND (%) | C = 38.1 |
| | H = 4.16 | | H = 4.2 |
| | N = 8.97 | | N = 10 |
| | S = 10.25 | | S = 10.16 |

EXAMPLE 4

Potassium β-(3-hydroxy-5-hydroxymethyl-2-methyl-4-pyridylmethylamino)ethanesulfonate 32 g (0.1 mole) of the finely-divided product of Example 3 are added to 150 cm$^3$ methanol. 2.7 g (0.05 mole) potassium borohydride are added, in small portions, with stirring, while maintaining the temperature at 20° C. After the borohydride is introduced, the mixture is stirred for 1 hour at 20° C., the insoluble matter filtered out and the filtrate concentrated to dryness. About 31 g of the product are obtained, which are recrystallised from 2 volumes of methanol. After filtration, 27 g (86%) of white crystals are obtained.

| ANALYSIS | | | |
|---|---|---|---|
| M.P. > 250° C. | | | |
| Soluble in water | | | |
| Insoluble in acetone | | | |
| CALCULATED (%) | C = 38.2 | FOUND (%) | C = 38.7 |
| | H = 4.77 | | H = 5.1 |
| | N = 8.91 | | N = 9 |
| | S = 10.19 | | S = 10.3 |

EXAMPLE 5

Sodium γ-(3-hydroxy-5-hydroxymethyl-2-methyl-4-pyridylmethyleneimino)propanesulfonate 13.9 g (0.1 mole) homotaurine are added to a solution of 4 g (0.1 mole) NaOH in 10 cm$^3$ water. Stirring is continued until complete dissolution, 150 cm$^3$ absolute ethanol are added, the mixture is heated to 60° C. to cause dissolution, and a single addition of 16.7 g (0.1 mole) finely-divided pyridoxal base is made. Precipitation follows dissolution. The mixture is stirred for a further 30 min. at 60° C., allowed to cool to 20° C. and dried at 5° C. The product is reslurried in absolute ethanol, dried and then oven-dried under vacuum at 60° C. 25.5 g (82%) of yellow crystals are obtained.

| ANALYSIS | | | |
|---|---|---|---|
| Soluble in water | | | |
| Insoluble in acetone and ethanol | | | |
| CALCULATED (%) | C = 42.55 | FOUND (%) | C = 43.1 |
| | H = 4.83 | | H = 4.97 |
| | N = 9.02 | | N = 9.1 |
| | S = 10.31 | | S = 10.4 |

EXAMPLE 6

Sodium γ-(3-hydroxy-5-hydroxymethyl-2-methyl-4-pyridylmethylamino)propanesulfonate 31 g (0.1 mole) of the finely-divided product of Example 5 are added to 150 cm$^3$ methanol. 1.8 g (0.05 mole) sodium borohydride are added, in small portions, with stirring, while maintaining the temperature at 20° C. After the borohydride is introduced, the mixture is stirred for 1 hour at 20° C., the insoluble matter filtered out and the filtrate concentrated to dryness. About 31 g of the product are obtained, which are recrystallised from 2 volumes of methanol. After filtration, 28 g (91%) of white crystals are obtained.

| ANALYSIS | | | |
|---|---|---|---|
| Soluble in water | | | |
| Insoluble in acetone | | | |
| CALCULATED (%) | C = 42.2 | FOUND (%) | C = 43.1 |
| | H = 4.79 | | H = 5.01 |
| | N = 8.95 | | N = 9.1 |
| | S = 10.23 | | S = 10.44 |

EXAMPLE 7

Potassium γ-(3-hydroxy-5-hydroxymethyl-2-methyl-4-pyridylmethyleneimino)propanesulfonate 13.9 g (0.1 mole) homotaurine are added to 6.16 g (0.11 mole) potash in 10 cm$^3$ water, with stirring. 150 cm$^3$ absolute ethanol are then added, when dissolution is complete. The mixture is heated to 60° C., and a single addition of 16.7 g (0.1 mole) finely-divided pyridoxal base is made. It dissolves. The mixture is kept for 30 min. at 60° C. Crystallisation is caused by scratching or seeding. The product is dried at 5° C., reslurried in absolute ethanol, and oven dried under vacuum at 60° C. 27.3 g (83.7% yield) of hygroscopic yellow crystals are obtained.

| ANALYSIS | | | |
|---|---|---|---|
| Soluble in water | | | |
| Insoluble in acetone | | | |
| CALCULATED (%) | C = 40.47 | FOUND (%) | C = 39.98 |
| | H = 4.59 | | H = 4.38 |
| | N = 8.58 | | N = 8.52 |
| | S = 9.01 | | S = 9.91 |

EXAMPLE 8

Potassium γ-(3-hydroxy-5-hydroxymethyl-2-methyl-4-pyridylmethylamino)propanesulfonate 32.6 g (0.1 mole) of the finely-divided product of Example 7 are added to 150 cm$^3$ methanol. 2.7 g (0.05 mole) potassium borohydride are added, in small portions with stirring, while maintaining the temperature at 20° C. After the borohydride is introduced, the mixture is stirred for 1 hour at 20° C., the insoluble matter is filtered out and concentrated to dryness. About 33 g of the product are obtained, which are recrystallised from 2 volumes of methanol. After filtration, 29.5 g (90%) of white cyrstals are obtained.

| ANALYSIS | | | |
|---|---|---|---|
| Soluble in water | | | |
| Insoluble in acetone | | | |
| CALCULATED (%) C = 40.22 | FOUND (%) | C = | 39.8 |
| H = 5.18 | | H = | 4.89 |
| N = 8.53 | | N = | 8.32 |
| S = 9.75 | | S = | 9.36 |

By the same procedure as that described for the sodium and potassium salts, salts of other alkali metals such as Li, Rb and Cs may be prepared.

EXAMPLE 9

Lithium β-(3-hydroxy-5-hydroxymethyl-2-methyl-4-pyridylmethyleneimino)ethanesulfonate 12.5 g (0.1 mole) taurine are added to 4.2 g (0.1 mole) LiOH in 10 cm³ water. The mixture is heated to 60° C. to cause dissolution and 150 cm³ absolute ethanol are added. The mixture is kept at 60° C., and 16.7 g (0.1 mole) finely-divided pyridoxal base are added. After heating for 30 min. at 60° C., the mixture is allowed to cool to 20° C. and then chilled at 0° C. The yellow precipitate is dried quickly and washed with 100 cm³ ethanol. It is then oven-dried at 60° C. 23.8 g are obtained, a 85% yield.

| ANALYSIS | | | |
|---|---|---|---|
| M.P. > 250° C. | | | |
| Soluble in water | | | |
| Insoluble in acetone | | | |
| CALCULATED (%) C = 42.8 | FOUND (%) | C = | 42.04 |
| H = 4.64 | | H = | 4.52 |
| N = 10 | | N = | 9.9 |
| O = 28.5 | | O = | 28.42 |
| S = 11.42 | | S = | 11.43 |
| Li = 2.5 | | Li = | 2.48 |

According to the same procedure, lithium γ-(3-hydroxy-5-hydroxymethyl-2-methyl-4-pyridylmethyleneimino)propanesulfonate, having a melting point higher than 250° C., is obtained; it is soluble in water and insoluble in acetone.

EXAMPLE 10

Lithium β-(3-hydroxy-5-hydroxymethyl-2-methyl-4-pyridylmethylamino)ethanesulfonate 28 g (0.1 mole) of the finely-divided product of Example 9 are added to 150 cm³ methanol. 1.1 g (0.05 mole) lithium borohydride are added, in small portions, with stirring, while maintaining the temperature at 20° C. The insoluble matter is filtered out and the filtrate concentrated to dryness. About 28 g of the product are obtained, which are recrystallised from 2 volumes of methanol. After filtration, 27 g (96%) of white crystals are obtained.

| ANALYSIS | | | |
|---|---|---|---|
| Soluble in water | | | |
| Insoluble in acetone | | | |
| CALCULATED (%) C = 42.5 | FOUND (%) | C = | 42.38 |
| H = 5.35 | | H = | 5.29 |
| N = 9.92 | | N = | 10 |
| O = 28.36 | | O = | 28.62 |
| S = 11.34 | | S = | 11.38 |
| Li = 2.48 | | Li = | 2.46 |

By the same procedure, lithium γ-(3-hydroxy-5-hydroxymethyl-2-methyl-4-pyridylmethylamino)propanesulfonate is obtained, which is soluble in water and insoluble in acetone.

Alkaline earth metal salts of the imino compounds are first formed by exchange between an alkali metal salt of an imino compound prepared as above, for example the sodium salt and an alkaline earth metal salt, e.g. an alkaline earth metal chloride. The imino compound is then reduced to the corresponding amino compound.

EXAMPLE 11

Calcium β-(3-hydroxy-5-hydroxymethyl-2-methyl-4-pyridylmethyleneimino)ethanesulfonate 26 g (0.0878 mole) of the compound of Example 1 are dissolved in 50 cm³ water. A solution of 6.5 g (0.0439 mole) anhydrous calcium chloride in 30 cm³ water is added all at once. The mixture is stirred for 30 min. and filtered through paper. The filtrate is concentrated to dryness. A red solid is obtained, which is dissolved in 100 cm³ methanol. Sodium chloride is filtered out and the filtrate is concentrated to dryness, and then oven-dried under vacuum. 25 g (97% yield) of an orange product are obtained.

| ANALYSIS | | | |
|---|---|---|---|
| M.P. > 250° C. | | | |
| Amorphous orange crystals | | | |
| Soluble in water | | | |
| Insoluble in acetone | | | |
| CALCULATED (%) C = 40.95 | FOUND (%) | C = | 41.2 |
| H = 4.43 | | H = | 4.5 |
| N = 9.55 | | N = | 9.6 |
| S = 10.92 | | S = | 11 |
| O = 27.3 | | | |
| Ca = 6.82 | | Ca = | 6.78 |

EXAMPLE 12

Calcium γ-(3-hydroxy-5-hydroxymethyl-2-methyl-4-pyridylmethyleneimino)propanesulfonate A solution of 3.7 g (0.025 mole) anhydrous calcium chloride in 20 cm³ water is added to a solution of 15.5 g (0.05 mole) of the sodium salt of Example 5 in 30 cm³ water. The mixture is stirred for 15 min. and a slight turbidity is filtered out. The filtrate is concentrated to dryness and then taken up to 100 cm³ boiling methanol. Sodium chloride is filtered out and the filtrate concentrated to dryness. 15.3 g (100% yield) of an orange salt are obtained.

| ANALYSIS | | | |
|---|---|---|---|
| Soluble in water | | | |
| Insoluble in acetone | | | |
| Soluble in methanol | | | |
| $C_{22}H_{30}N_4S_2O_{10}Ca = 614.32$ | | | |
| CALCULATED (%) C = 42.97 | FOUND (%) | C = | 43.01 |
| H = 4.88 | | H = | 4.91 |
| N = 9.11 | | N = | 9.08 |
| S = 10.41 | | S = | 10.38 |
| Ca = 6.51 | | Ca = | 6.49 |

-continued

Residual water content = 3.7%

EXAMPLE 13

Magnesium
β-(3-hydroxy-5-hydroxymethyl-2-methyl-4-pyridylmethyleneimino)ethanesulfonate 29.6 g (0.1 mole) of the sodium salt of Example 1 are suspended in 180 cm$^3$ methanol. A solution of 10.2 g (0.05 mole) hydrated magnesium chloride in 20 cm$^3$ methanol is then added. There is almost complete dissolution, and precipitation of sodium chloride. The mixture is stirred for 30 min. and filtered. The filtrate is concentrated to dryness and desiccated under vacuum. The solid is taking up in 100 cm$^3$ boiling methanol and heat-dried. Oven-drying under vacuum at 80° C. follows. 27 g (95%) of amorphous orange product are obtained.

| ANALYSIS | | | | | |
|---|---|---|---|---|---|
| Soluble in water | | | | | |
| Insoluble in methanol and acetone | | | | | |
| CALCULATED (%) | C = | 42 | FOUND | C = | 41.4 |
| | H = | 4.56 | (%) | H = | 5.02 |
| | O = | 28 | | O = | 27.8 |
| | N = | 9.8 | | N = | 9.8 |
| | Mg = | 4.26 | | Mg = | 4.02 |
| Water content < 2% | | | | | |

EXAMPLE 14

Magnesium
γ-(3-hydroxy-5-hydroxymethyl-2-methyl-4-pyridylmethyleneimino)propanesulfonate 31 g (0.1 mole) of the sodium salt of Example 5 are suspended in 180 cm$^3$ methanol. A solution of 10.2 g (0.05 mole) magnesium chloride hydrate in 20 cm$^3$ methanol is then added. There is almost complete dissolution, and precipitation of sodium chloride. The mixture is stirred for 30 min. and filtered. The filtrate is concentrated to dryness and desiccated under vacuum. The solid is taken up in 100 cm$^3$ boiling methanol and dried by heating. Oven-drying under vacuum at 80° C. follows. 29 g (97%) of amorphous orange product are obtained.

| ANALYSIS | | | | | |
|---|---|---|---|---|---|
| Soluble in water | | | | | |
| Insoluble in methanol and acetone | | | | | |
| CALCULATED (%) | C = | 44.1 | FOUND | C = | 43.9 |
| | H = | 5 | (%) | H = | 4.85 |
| | N = | 9.35 | | N = | 9.48 |
| | O = | 26.7 | | O = | 27 |
| | Mg = | 4.06 | | Mg = | 3.72 |
| Water content < 2% | | | | | |

By the same procedure as that described for the Ca and Mg salts, salts of other alkaline earth metals such as Sr, Ba, etc. can be prepared.

Evidence of cation vector properties

This study compares the ratios (B/P) between oral toxicity (LD$_{50}$ by gastric tubage=B) and parenteral toxicity (LD$_{50}$ i.p.=P) of the alkali metal or alkaline earth metal salts with that of reference salts (corresponding alkali metal or alkaline earth metal chlorides) in order to show surprisingly that the B/P ratio, for each cation, is clearly preferable, i.e. significantly lower than that for the corresponding reference salt.

Magnesium salts

The study is carried out with Swiss I.O.P.S. mice, in lots of 20 animals of both sexes. The B/P ratio for the reference salt, MgCl$_2$, expressed in mmol/kg is 19.2/9.4=2.04. For Mg salts of the invention, i.e. those of Examples 13 and 14, it is considerably, and highly significantly, reduced (p<0.01 analytical variance) with respect to the reference salt, i.e. respectively 3.3/2.8=1.17 and 4.1/3.3=1.24. By contrast, these results are not significantly mutually different.

The Mg salts of the invention are thus, according to this test, active by both the oral and parenteral routes, which is quite exceptional for a magnesium salt.

It has been determined that this discovery is not appropriate to a particular animal, by making the same observation for the Sprague-Dawley I.O.P.S. rat where the B/P ratio for magnesium chloride is greater than 39.3/4.4=8.99. For the respective compounds of Examples 13 and 14, the ratio is reduced in a most significant manner (p<0.001), to 3.3/2.2=1.5 and 4.2/2.4=1.66.

This again verifies the exceptional efficacity, by this test, of Mg salts of the invention, while the ratios for the two compounds (imino and amino) are not mutually significantly different in the two animal species.

Calcium salts

Parallel discoveries have been made for the Ca salts. For example, in the Swiss I.O.P.S. mouse, the B/P ratio of CaCl$_2$ is greater than 36.5/3.9=9.2. It is reduced, respectively, for the salts of Examples 11 and 12 to 7.7/2.6=2.96 and to 8.1/2.4=3.3. Again, the reduction is not mutually significantly different for the two salts.

Potassium salts

Parallel discoveries have been made for the potassium salts. In the Swiss I.O.P.S. mouse, the ratio for potassium chloride (reference salt) is greater than 107.3/14.8=7.25. It is reduced for the imino compounds of Examples 3 and 7, respectively to 7.0/3.9=1.79 and 7.0/4.0=1.75; for the compounds of Examples 4 and 8, the ratios are respectively 15.7/13.0=1.20 and 17.0/14.2=1.19. Again, there is a very considerable, significant reduction (p<0.001) of the B/P ratio, evidence of the efficacity of the compounds. Further, it should be noted that the amino compounds possess, like the imino compounds, the unexpected vector properties. The ratios for the four compounds of the Examples above, i.e. the imino and amino compounds, is not mutually significantly different.

Sodium salts

While the ratio for the reference salt, sodium chloride, is greater than 205.4/61.2=3.36, it is, for the imino compounds of Examples 1 and 5 7.0/3.0=2.33 and 6.7/4.4=1.52, respectively, and, for the amino compounds of Examples 2 and 6 (while not strictly determined but without doubt greater than 1), respectively greater than 20.1/20.1=1 and greater than 19.2/13=1.43. Again, the imino and corresponding amino compounds possess the same cationic vector properties.

The high cell penetration of the compounds of the invention is not only evident from their advantageous B/P ratio. This property is equally evident from the results of pharmacological activity tests.

By way of example, the compounds are tested, on one hand by the test of Macallum et al., Can. Chem. Process Industries 26 (1942) 569, which studied the potentiation of insulin by sulfones in the rabbit and, on the other hand, by the test of Fariello et al., Neurology 30 (1980) 386, in which the authors showed that homotaurine antagonises the neurotoxic or convulsant activity of kainic acid administered systemically to the rat.

By the first test, it has been found that the compounds of the invention, administered orally, potentiate the hypoglycemic activity of an intravenous, non-convulsant dose of insulin, although taurine and homotaurine, which are active intravenously, are not orally active.

In the second test, while taurine and homotaurine, administered per os, cause no significant reduction of the neurotoxic effect of kainic acid (symptom observed: "wet dog shaking"), the compounds of the invention, administered by the same route, clearly exhibit activity.

After these tests, the one metabolic and the other neurologic, compounds of the invention can be seen to be significantly active orally, while taurine, homotaurine, vitamin B6 and the cationic reference salts corresponding to the salts of the invention are inactive by this route.

The range of compounds of the invention, both imino and amino, salts of magnesium, calcium, lithium, potassium and sodium all exhibit exceptional efficacy buccally, almost equal to that by the parenteral route in the best cases, and an efficacity one-third of that by the parenteral route in the least good cases. It is nevertheless significantly greater, in all cases, than that of the salts of corresponding reference cations, i.e. the corresponding chlorides.

Therapeutic Applications

The cationic vector properties can be used to cause penetration of the respective cations, in all cases where there is a loss of ions, which are refractory to conventional therapy. The sodium, potassium, lithium, calcium and magnesium salts of the invention can be used to alleviate loss of the corresponding cations, in cases refractory to conventional treatment. Magnesium losses, in particular, often do not respond to magnesotherapy. In therapy, hitherto, magnesium salts are poorly absorbed and penetrate the cell wall poorly. The loss of magnesium in erythrocytes, used as evidence of intracellular loss, is frequently resistant to the recharging of magnesium.

Now, in magnesium deficiency, on a regime of only 25 ppm of magnesium in Sprague-Dawley I.O.P.S. rats, the efficacity of the salts of Examples 13 and 14 in effecting the recharge of magnesium by the oral route, has been shown for these two salts in a variety of ways. For example, reduced aggression of deficient rats with respect to mice (reduction in muricide activity) can be demonstrated but, unpredictably, it has been possible to show with various posologies (strong: 40 mg magnesium/kg/day, median: 20 mg magnesium/kg/day and weak; 5 mg magnesium/kg/day) a primary effect in correction of reduction in erythrocyte magnesium with relation to that of plasma magnesium. This cannot be explained by selective penetration of magnesium salts of the invention across the red globule membrane. The correction can be observed on the first day; hypercorrection can be observed on the third day (respectively 79.2 mg for the compound of Example 13 and 75.8 mg for the compound of Example 14). The deficient animals have a level of 40 mg and the control animals 60 mg.

By contrast, at the doses previously tested, the correction in reduction of plasma magnesium in experimentally subacute deficiency is never produced before the third day of administration of the compounds. These delays are always shorter than those observed with the reference magnesium salt (magnesium chloride).

Other Properties

The systemic cationic vector properties of the compounds of the invention do not exclude other particular therapeutic uses of these compounds. Certain properties can vary considerably according to the structure of the anion, particularly whether or not saturated, and the nature of the cation.

For example, one can see across the scope of compounds of the invention, only one, i.e. the compound of Example 8, which has an activity similar to that of taurine but considerably potentiated, i.e. 17 times more active, in the test of Frances et al., Prog. Neuropsychopharmacol. 1 (1977) 227–230. The results are shown in the following Table:

| Compound | $ED_{50}$ rolling | $ED_{50}$ trembling |
| --- | --- | --- |
| Taurine | 4.67 mmol/kg | 4.34 mmol/kg |
| Compound of Example 8 | 0.27 mmol/kg | 0.27 mmol/kg |

Galenic Form

If the water-solubility of compounds of the invention allows parenteral administration, in ampoules designed for the subcutaneous, intramuscular and intravenous routes, the preferred route of administration is oral, and any galenic form may be used, i.e. compressed tablet, coated pill, granulate, solution, syrup, etc. Suppositories and forms for local administration of these products of high cell penetration, such as collyria, nasal or ear drops, ointments, etc. are not excluded.

By way of example of a galenic preparation, a conventional galenic procedure may be used to prepare gelatine-coated pills containing 250 mg of the compound of Example 13, drinkable ampoules of 5 ml containing 200 mg of the compound of Example 12, and 10% aqueous solutions of the compound of Example 8. The unit dosage of these various compositions may be from 10 to 1000 mg.

Example of Therapeutic Use

Madam Ser . . . Claude was attacked by latent tetany by magnesium deficiency. She was treated for two years by various forms of magnesotherapy: 3 g magnesium lactate per day or three drinkable ampoules of magnesium pyroglutamate (standardised 127 mg $Mg^{2+}$ per ampoule) per day, without succeeding in correcting an erythrocyte magnesium level varying from 43 to 46 mg/l. A prescription of 3 gelatine-coated pills of the compound of Example 13 led to a regression of chemical symptoms (headache, asthenia, cramp) and the increase, to 48 mg/l in the first month and to 53 mg/l in the second month, of the erythrocyte magnesium level. Ultimately, it was nevertheless observed that each interruption in administration of the product was followed, in the subsequent chemical and biological monthly control, by a relapse (comprising the symptomotology and reduction of the erythrocyte magnesium level to about 45 mg/l). In summary, a daily input of 32 mg magnesium ion in the form of 750 mg of the compound of Example 13 is shown to be more active in controlling magnesium deficiency which is refractory to the prescription of conventional magnesium salts at doses 10 times larger.

What is claimed is:

1. A method of treating deficiencies of metal ions in humans or animals in need of such treatment comprising the oral or parenteral administration of an effective amount of salt of formula (I):

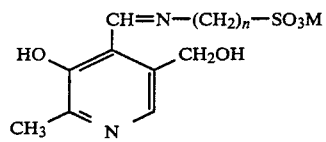

or a salt of formula (II):

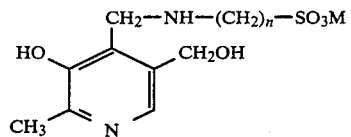

wherein n is 2 or 3 and M is an alkali metal or an alkaline earth metal.

2. The method of claim 1, wherein n is 2 and M is selected from Na, K, Li, Ca and Mg.

3. The method of claim 1, wherein n is 3 and M is selected from Na, K, Li, Ca and Mg.

4. The method of claim 1, wherein n is 2 and M is selected from Na, K and Li.

5. The method of claim 1, wherein n is 3 and M is selected from Na and K.